United States Patent

Panzera et al.

[11] Patent Number: 6,087,282
[45] Date of Patent: Jul. 11, 2000

[54] NON-GREENING PORCELAIN COMPOSITIONS

[75] Inventors: Carlino Panzera, Belle Mead; Dmitri Brodkin, West Orange; Paul Panzera, Mt. Holly, all of N.J.

[73] Assignee: Jeneric/Pentron Incorporated, Wallingford, Conn.

[21] Appl. No.: 09/113,419

[22] Filed: Jul. 10, 1998

[51] Int. Cl.[7] .......................... A61C 13/083; C03C 8/02; C03C 3/091; C03C 3/083; C03C 3/118
[52] U.S. Cl. ................... 501/21; 106/35; 501/59; 501/63; 501/64; 501/66; 501/68; 501/69; 501/70; 501/72; 433/202; 433/216; 433/212.1; 427/2.29
[58] Field of Search .......................... 106/35; 433/202.1, 433/206, 212.1; 501/59, 63, 64, 66, 68, 69, 70, 72, 21; 427/2.27, 2.26, 2.29

[56] References Cited

U.S. PATENT DOCUMENTS

| | | |
|---|---|---|
| 4,405,300 | 9/1983 | Lubowsky et al. . |
| 4,806,507 | 2/1989 | Olby . |
| 5,030,097 | 7/1991 | Tobey . |
| 5,281,563 | 1/1994 | Komma et al. . |
| 5,308,391 | 5/1994 | Komma et al. ........................ 501/66 |
| 5,346,866 | 9/1994 | Komma et al. . |
| 5,382,552 | 1/1995 | Saad et al. . |
| 5,389,402 | 2/1995 | Speer et al. . |
| 5,466,285 | 11/1995 | Kamiya et al. ........................ 106/35 |
| 5,552,350 | 9/1996 | Hornor .................................. 501/66 |
| 5,653,791 | 8/1997 | Panzera et al. ........................ 106/35 |

OTHER PUBLICATIONS

Obrien WJ, Boenke KM, Linger JB, Groh CL; *Cerium Oxide as a Silver Decolorizer in Dental Porcelains*; Dental Materials 14:365–369, Sep., 1998.

*Primary Examiner*—C. Melissa Koslow
*Attorney, Agent, or Firm*—Ann M. Knab

[57] ABSTRACT

Porcelain compositions of the present invention possess non-greening properties and comprise one or more glass or glass-ceramic components. Additionally, an oxygen release agent is included in the compositions. The porcelain compositions may vary depending upon the specific thermal properties desired.

The application temperature of the porcelain compositions ranges from about 600° C. to about 930° C. depending upon the method of application of the porcelain. The coefficient of thermal expansion is preferably in the range of about $11 \times 10^{-6}$/° C. to about $16 \times 10^{-6}$/° C. The porcelain is compatible with cores and/or substrates having coefficients of thermal expansion in the range of about 11 to about $20 \times 10^{-6}$/° C.

8 Claims, No Drawings

NON-GREENING PORCELAIN COMPOSITIONS

TECHNICAL FIELD

The present invention relates generally to porcelain compositions and more specifically to dental porcelain compositions useful in the preparation of dental restorations.

BACKGROUND OF THE INVENTION

Metal alloys have been employed in the dental industry for many, many years in the fabrication of crowns, bridges and other prosthetic appliances. In order to reduce the high cost involved in using gold and platinum in the manufacture of dental appliances, silver became a popular and inexpensive metal substitute. Furnaces employed in the preparation of dental restorations are typically used for a large variety of dental restorations irrespective of the alloy type. Although using the furnace for the heating of a variety of materials is considered an efficient utilization thereof, problems arise due to the contamination of the furnace interior with residue from the processing occurring therein.

One specific problem arises from silver and/or copper impurities remaining on the furnace interior after the firing of porcelain or silver containing alloys. It is speculated that silver impurities present in the furnace during the firing of ceramic material cause discoloration in the resultant porcelain material. This discoloration is also referred to as "greening" and is believed to occur when silver appears in glass as $Ag^0$. Maintenance and cleaning of furnaces by scrubbing, purging and the like have helped to reduce the greening effect, but have not been either totally effective or completely efficient. One known method discussed in U.S. Pat. No. 4,405,300 to Lubowsky et al. uses carbon as an absorbent. Carbon is positioned in an empty, contaminated furnace and a firing cycle is completed in the furnace. The carbon absorbs contaminants in the furnace and thereby, the furnace is cleansed and purged of impurities. This method is effective, but is inefficient and inconvenient since the furnace and operator must partake in unproductive and unprofitable firing cycles. This purging process must be performed frequently to provide consistency in the quality of the ceramic restorations produced.

Another form of discoloration or "greening" in dental restorations can occur from the alloy coping itself when it is composed of silver, copper or some other alloy that may form reduced metal ($Me^0$) clusters in overlay porcelain.

High fusion temperature porcelains having non-greening properties have been developed and are currently in use. These porcelains are typically utilized as body porcelains because they tend not to be translucent enough for the outer layers of the restorations. It is often necessary to increase the opacity of these porcelains to mask their sometimes speckled appearance.

There is a need to provide low fusing porcelain compositions that do not discolor when fired in contaminated furnaces or applied on silver or copper containing metal copings. It is advantageous that the firing furnace be used to its full potential. There is a need to provide low fusing porcelains which are transparent and do not discolor.

SUMMARY OF THE INVENTION

These and other objects and advantages are accomplished by the porcelain compositions of the present invention that possess non-greening properties and comprise one or more glass and/or glass-ceramic components and an oxygen release agent.

The compositions prevent greening in porcelain occurring from the silver impurities present in the furnace and/or from silver or copper containing metal copings. It has been found that the addition of the oxygen release agent to the raw materials used in making the porcelain compositions later prevents greening or discoloration of the porcelain. The oxygen release agent releases oxygen or oxidizing gases when the components in the glass are melted together. The temperature employed to melt the glass is high enough to obtain a homogeneous melt and low enough to retain residual oxygen in the glass melt or trap bubbles therein. The resultant low-fusing porcelain powders have an oxygen potential high enough to keep silver impurities in the oxidized state and/or to prevent silver from entering glass in the reduced state.

The porcelain compositions possess a maturing temperature in the range of about 600° C. to about 930° C. depending upon the method of application of the porcelain. The coefficient of thermal expansion is preferably in the range of about $11 \times 10^{-6}$/° C. to about $16 \times 10^{-6}$/° C. However, as glazes, these porcelains can be used on substrates having coefficients of thermal expansion in the range of about $11 \times 10^{-6}$/° C. to about $20 \times 10^{-6}$/° C.

In one embodiment of the method of the present invention, various oxides or precursors thereof along with an oxygen release agent are mixed together and melted to prepare a porcelain frit. In another embodiment of the present invention, one or more glass and/or glass-ceramic frit compositions are mixed together, an oxygen release agent is added and the mixture is melted together to form a porcelain frit.

DETAILED DESCRIPTION OF THE INVENTION

The present invention is directed to porcelain compositions that can be used to form dental restorations in accordance with known procedures. Preferably, the porcelain compositions can be employed as glaze on a metal framework in porcelain fused to metal (PFM) restorations or on a ceramic framework in all-ceramic restorations such as those manufactured using Synspar®, Pencraft Plus™, OPC® and Optec® ceramic systems all available from Jeneric/Pentron, Wallingford, Conn. The porcelain compositions of the present invention are also useful as transparent add-on, incisal, and overlay porcelains.

The porcelain compositions possess a maturing temperature in the range of about 600° C. to about 930° C. depending upon the method of application of the porcelain. For example, if the porcelain is being used as incisal or add-on porcelain, the maturing temperature will range from about 600° C. to about 880° C. If the porcelain is being used as a glaze, the glazing temperature will range from about 700° C. to about 930° C., depending upon the substrate porcelain. The coefficient of thermal expansion is preferably in the range of about $11 \times 10^{-6}$/° C. to about $16 \times 10^{-6}$/° C. However, if the porcelain is used as a glaze, it can be used on substrates having coefficients of thermal expansion in the range of about $11 \times 10^{-6}$/° C. to about $20 \times 10^{-6}$/° C. The properties can be adjusted by applying well known techniques in the industry. For example, the coefficient of thermal expansion can be increased by decreasing the amount of $SiO_2$ with respect to the alkali metal oxides or increasing the amount of alkali metal oxides with respect to $SiO_2$. The maturing temperature can be reduced by increasing the amount of CaO and/or the alkali metal oxides. A different combination of fluxes can be used to achieve the same reduction in glass viscosity which in turn results in a lower maturing temperature. The metal and ceramic frameworks are the core components in the dental restorations being fabricated. For example, various combinations of acidic fluxes such a $B_2O_3$, $P_2O_5$, and F can be used, or various combination of alkali ($Li_2O$, $Na_2O$, $K_2O$) and alkaline earth oxide (CaO and BaO) fluxes can be used interchangeably with the aforementioned fluxes.

The porcelain compositions may comprise the following components in the following ranges:

from about 57% to about 68% by weight $SiO_2$;

from about 2% to about 13% by weight $Al_2O_3$;

from about 20% to about 35% by weight of a flux comprising $R_2O+RO$, wherein $R_2O$ is at least one of $Na_2O$, $Li_2O$, $K_2O$ and mixtures thereof, and wherein RO is at least one of CaO, MgO, BaO and mixtures thereof;

from about 0.5% to about 7% by weight of a flux comprising at least one of $B_2O_3$ F and $P_2O_5$; and from about 0.1% to about 2% of an oxygen release agent.

Preferably, the porcelain composition contains the following components in the following ranges:

from about 57% to about 68% by weight $SiO_2$;

from about 2% to about 13% by weight $Al_2O_3$;

from about 4% to about 15% by weight $Na_2O$;

up to about 4% $Li_2O$;

up to about 5% by weight $B_2O_3$;

up to about 3% F;

up to about 3% $P_2O_5$;

wherein the total of $B_2O_3$, $P_2O_5$ and F is from about 0.8% to about 7% by weight;

from about 0.1% to about 1% of an oxygen release agent;

up to about 15% $K_2O$;

up to about 6% by weight CaO;

up to about 5% by weight MgO; and up to about 3% BaO.

More preferably, the porcelain composition contains the following components in the following ranges:

from about 57% to about 67% by weight $SiO_2$;

from about 2% to about 10% by weight $Al_2O_3$;

from about 7% to about 15% by weight $Na_2O$;

from about 0.4% to about 3% $Li_2O$;

up to about 2% by weight $B_2O_3$;

up to about 2% F;

up to about 2% $P_2O_5$;

wherein the total of $B_2O_3$, $P_2O_5$ and F is from about 1% to about 4% by weight;

from about 0.1% to about 1% of an oxygen release agent;

from 0.1% to about 14% $K_2O$;

up to about 5% by weight CaO;

up to about 4% by weight MgO; and up to about2% BaO.

The compositions prevent greening in the porcelain occurring from the Ag impurities present in the furnace. The addition of oxygen release agents to the raw materials used in making the porcelain compositions was found to prevent greening. The oxygen release agents release oxygen or oxidizing gases when the components in the glass are melted together. Oxygen release agents used in the invention are those known in the art and include but are not limited to $Sb_2O_3$, $CeO_2$, $KNO_3$, $NaNO_3$ and other compounds known to release oxygen or oxidizing gases (e.g., $NO_2$) at glass melting temperatures. The temperature employed to melt the glass is high enough to obtain a homogeneous melt and low enough to retain residual oxygen in the glass melt or trap bubbles therein.

In accordance with a method of making the porcelain of the present invention, raw materials such as feldspar, alkali and alkaline-earth carbonates, silicates, alumina and silica are combined to form the composition within the ranges set forth above. An oxygen release agent is also added to the mixture of raw materials. Combinations of oxygen release agents can be used as well, such as for example, $Sb_2O_3$ and $NaNO_3$. The raw materials are then heated to a temperature in the range of about 1000° C. to about 1300° C. to form a homogeneous melt. The resultant glass is pulverized or milled into a powder and sieved to the required mesh size. It may be further mixed with other frits, pigments and fluorescing agents to obtain the desired porcelain powder. The resultant low-fusing porcelain powders have an oxygen potential high enough to keep silver impurities in the oxidized state and/or to prevent silver from entering glass in the reduced state. The porcelain may be used to make a dental restoration by applying a porcelain layer onto a core component such as a metal or ceramic framework. The porcelain is then fired at a temperature for a period of time to form a veneering layer, wherein the porcelain has non-greening properties. Preferably, the porcelain is fired at a temperature in the range of from about 600° C. to about 800° C. when either ceramic or metal frameworks are used.

The following examples illustrate the practice of the invention.

EXAMPLES 1–7

The glass powder compositions listed in Table 1 were prepared by melting glass precursor components together and heating in the range of 1000° C. to 1100° C. The glass melt was furnace cooled and ground to a powder and sieved to −400 mesh particle size. The compositions listed in Table 1 are calculated based on the starting batch compositions. Actual fluorine content may therefore be significantly lower due to volatilization losses during melting. The exact percentages of other components such as $Li_2O$ and $B_2O_3$ may also deviate slightly from these calculated values. In the practice of the invention, other components may or may not be present depending on the particular use and physical requirements of the porcelain. The powder was applied on silver coupons and fired at 1740° F. (950° C.). The samples were visually inspected for the presence of discoloration associated with silver contamination. None of the samples showed significant discoloration or greening.

TABLE 1

| component | 1 | 2 | 3 | 4 | 5 | 6 | 7 |
|---|---|---|---|---|---|---|---|
| $SiO_2$ | 64.7 | 64.7 | 62.9 | 64.6 | 66.6 | 64.5 | 64.5 |
| $B_2O_3$ | — | — | 1.7 | 1.7 | 2.0 | — | — |
| $Al_2O_3$ | 8.3 | 8.3 | 9.1 | 6.0 | 2.9 | 8.5 | 8.5 |
| CaO | 1.2 | 1.2 | 1.8 | 2.0 | 4.9 | 1.4 | 1.4 |
| MgO | 1.1 | 1.1 | 1.0 | 0.7 | 3.9 | 1.1 | 1.1 |
| BaO | — | — | — | — | 1.96 | — | — |
| $Li_2O$ | 1.2 | 1.2 | 1.1 | 1.5 | 1.1 | 0.9 | 0.9 |
| $K_2O$ | 13.5 | 13.5 | 10.6 | 11.0 | 1.0 | 12.4 | 12.4 |
| $Na_2O$ | 8.9 | 8.9 | 11.0 | 11.3 | 14.7 | 8.7 | 8.7 |
| F | 2.0 | 2.0 | 1.4 | 1.9 | 1.5 | 1.4 | 1.4 |
| $P_2O_5$ | — | — | — | — | — | 0.5 | 1.0 |
| $Sb_2O_3$ | 0.4 | — | 0.4 | 0.4 | 0.4 | 0.4 | 0.4 |
| *$CeO_2$ | — | 0.4 | — | — | — | — | — |

TABLE 1-continued

| component | 1 | 2 | 3 | 4 | 5 | 6 | 7 |
|---|---|---|---|---|---|---|---|
| $B_2O_3 + P_2O_5 + F$ | 2.0 | 2.0 | 3.1 | 3.6 | 3.4 | 1.9 | 2.4 |
| $CTE_{(10^{-6}/°C.)}$ (25° C.–470° C.) | 12.8 | 12.8 | 12.7 | 14.2 | 12.1 | — | — |

*added initially, may transform fully or partially into $Ce_2O_3$

As will be appreciated, the present invention provides porcelain compositions having greening resistance particularly for use in the fabrication of dental restorations. The porcelains in accordance with the present invention are especially suitable for use in dental restorations as a glaze layer on top of a PFM restoration or an all ceramic restoration. The porcelains may also be utilized as non-greening add-on, incisal, and low fusing porcelains in the manufacture of dental restorations.

While various descriptions of the present invention are described above, it should be understood that the various features can be used singly or in any combination thereof Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A low-fusing porcelain composition having non-greening properties comprising;
   from about 57% to about 68% by weight $SiO_2$;
   from about 3% to about 13% by weight $Al_2O_3$;
   from about 20% to about 35% by weight of a flux comprising $R_2O+RO$, wherein $R_2O$ is at least one of $Na_2O$, $Li_2O$, $K_2O$ and mixtures thereof, and wherein RO is at least one of CaO, MgO, BaO and mixtures thereof;
   from about 0.8% to about 7% by weight of a flux comprising at least one of $B_2O_3$, F and $P_2O_5$; and
   from about 0.1% to about 2% of an oxygen release agent; whereby the oxygen release agent is an alkali nitrate.

2. The composition of claim 1 wherein the alkali nitrate is $KNO_3$ or $NaNO_3$.

3. A low-fusing porcelain composition having non-greening properties comprising;
   from about 57% to about 68% by weight $SiO_2$;
   from about 2% to about 13% by weight $Al_2O_3$;
   from about 4% to about 15% by weight $Na_2O$; and
   from about 0.1% to about 2% of an oxygen release agent; whereby the oxygen release agent is an alkali nitrate.

4. The composition of claim 3 wherein the alkali nitrate is $KNO_3$ or $NaNO_3$.

5. A low-fusing porcelain composition having non-greening properties comprising;
   from about 57% to about 67% by weight $SiO_2$;
   from about 2% to about 10% by weight $Al_2O_3$;
   from about 7% to about 15% by weight $Na_2O$;
   from about 0.4% to about 3% by weight $Li_2O$;
   from 0.1% to about 14% by weight $K_2O$; and
   from about 0.1% to about 2% by weight of an oxygen release agent; whereby the oxygen release agent is an alkali nitrate.

6. The composition of claim 5 wherein the alkali nitrate is $KNO_3$ or $NaNO_3$.

7. A dental restoration having a glaze comprising:
   a low-fusing porcelain composition having non-greening properties whereby the porcelain is formed by the process comprising mixing glass precursor components together with an oxygen release agent; heating the mixture to a temperature in the range of about 1000° C. to about 1100° C. for a period of time to melt the components and agent; and cooling the mixture to form the porcelain composition.

8. A method of making a dental restoration comprising:
   forming a porcelain having non-greening properties whereby the porcelain is formed by the process comprising mixing glass precursor components together with a oxygen release agent and heating to a temperature in the range of 1000° C. to 1100° C. and cooling to form the porcelain composition;
   applying the porcelain as a layer onto a core component selected from the group consisting of a metal and ceramic framework, wherein the framework has a coefficient of thermal expansion between about 11 and $20 \times 10^{-6}/°$ C.;
   firing at a temperature between about 700° C. to about 930° C. for a period of time to form a glaze, wherein the glaze has non-greening properties.

* * * * *